(12) United States Patent
Oftring et al.

(10) Patent No.: US 8,802,894 B2
(45) Date of Patent: Aug. 12, 2014

(54) PROCESS FOR THE PREPARATION OF AQUEOUS SOLUTIONS OF METHYLGLYCINE-N,N-DIACETIC ACID TRIALKALI METAL SALTS

(75) Inventors: Alfred Oftring, Bad Duerkheim (DE); Gerold Braun, Ludwigshafen (DE); Arnulf Lauterbach, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 214 days.

(21) Appl. No.: 13/431,381

(22) Filed: Mar. 27, 2012

(65) Prior Publication Data
US 2012/0248370 A1 Oct. 4, 2012

(30) Foreign Application Priority Data
Feb. 7, 2012 (EP) ..................................... 12154201

(51) Int. Cl.
*C07C 227/18* (2006.01)
(52) U.S. Cl.
USPC .......................................................... 562/571
(58) Field of Classification Search
CPC .............................. C07C 227/26; C07C 253/06
See application file for complete search history.

(56) References Cited

U.S. PATENT DOCUMENTS

| | | | |
|---|---|---|---|
| 3,733,355 A | 5/1973 | Harris et al. | |
| 5,786,313 A | 7/1998 | Schneider et al. | |
| 5,817,864 A | * 10/1998 | Greindl et al. | ................. 560/171 |
| 5,849,950 A | 12/1998 | Greindl et al. | |

FOREIGN PATENT DOCUMENTS

| | | |
|---|---|---|
| DE | 2 027 972 | 4/1971 |
| DE | 43 19 935 A1 | 12/1994 |
| EP | 0 745 582 A2 | 12/1996 |
| GB | 1 284 635 | 8/1972 |
| WO | WO 94/29421 | 12/1994 |
| WO | WO 2011/042836 A1 | 4/2011 |

OTHER PUBLICATIONS

Zuend et al, Nature, Scaleable Catalytic Asymmetric Strecker Syntheses of Unnatural alpha-Amino Acids, 2009, 461(7266), pp. 968-970.*
Zaragoza Dorwald (Side Reactions in Organic Synthesis, 2005, Wiley-VCH Verlag GmbH & Co. KGaA, Weinheim, Preface. p. IX.*
U.S. Appl. No. 13/430,105, filed Mar. 26, 2012, Baumann, et al.
U.S. Appl. No. 13/498,825, filed Mar. 28, 2012, Judat, et al.
U.S. Appl. No. 13/463,446, filed May 3, 2012, Oftring, et al.
U.S. Appl. No. 13/720,027, filed Dec. 19, 2012, Bouchedid, et al.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

A process for preparing an aqueous solution of a methylglycine-N,N-diacetic acid trialkali metal salt at a high yield and purity by Strecker synthesis, the process including: reacting an aqueous solution containing α-alanine with formaldehyde and hydrocyanic acid, to obtain α-alanine-N,N-diacetonitrile in one reaction unit; and saponification of the α-alanine-N,N-diacetonitrile with a base, to obtain the methylglycine-N,N-diacetic acid trialkali metal salt, wherein the α-alanine is partially neutralized and the addition of formaldehyde and hydrocyanic acid are controlled such that a concentration of free hydrocyanic acid in the liquid reaction mixture at any time is limited such that secondary reactions that produce formaldehyde cyanohydrin, consecutive reactions of formaldehyde cyanohydrin, and the polymerization of hydrocyanic acid, only occur insofar as the specification requirements, such as nitrilotriacetic acid content and color, for methylglycine-N,N-diacetic acid trialkali metal salts are observed.

20 Claims, No Drawings

PROCESS FOR THE PREPARATION OF AQUEOUS SOLUTIONS OF METHYLGLYCINE-N,N-DIACETIC ACID TRIALKALI METAL SALTS

This patent application claims the benefit of pending U.S. provisional application Ser. No. 61/471,240 filed on Apr. 4, 2011, and EP patent application EP 12 154 201.3 filed on Feb. 7, 2012, incorporated in their entirety herein by reference.

The invention relates to a process for the preparation of aqueous solutions of methylglycine-N,N-diacetic acid trialkali metal salts.

The substances often used as complexing agents in cleaners, such as aminopolyphosphonates, polycarboxylates or aminopolycarboxylates, for example ethylenediaminetetraacetic acid (EDTA), are either only biodegradable with difficulty or, as in the case of nitrilotriacetic acid (NTA), toxic. For NTA, renal carcinogenicity is suspected.

A cost-effective alternative to this is α-alanine-N,N-diacetic acid (methylglycine-N,N-diacetic acid, referred to below in abbreviated form as MGDA), which is non-toxic and readily biodegradable.

The use of MGDA and its salts as complexing agents and also its syntheses are described in various patent applications from BASF SE, for example in DE-A 43 19 935 or in EP-A 0 745 582.

An economical and simultaneously environment-protecting synthesis route for the preparation of MGDA is the Strecker synthesis. The Strecker synthesis of MGDA is described, for example, in WO-A 1994/29421.

DE-A 20 27 972 describes the "acidic" variant of the Strecker reaction of glycine, the simplest unsubstituted α-aminocarboxylic acid, with formaldehyde and hydrocyanic acid. In this, glycine forms N,N-bis(cyanomethyl)glycine, which can be isolated in high purity. A disadvantage of the described process is the required use of additional acid for lowering the pH, and also the use of relatively expensive pure glycine. The glycine-N,N-diacetonitrile which is formed in the reaction is described for use as crosslinker. The possible saponification to give nitrilotriacetic acid is not subject matter of DE-A 20 27 972.

The reaction of alanine by means of Strecker reaction to give MGDA is described for the first time in WO-A 1994/29421, MGDA being obtained here by saponification in high yields with high purity.

The "alkaline" variant of the Strecker reaction is described for example in U.S. Pat. No. 3,733,355 in general form. However, the examples listed therein indicate that a high fraction of by-products, primarily of undesired nitrilotriacetic acid (NTA), always arises; this can be concluded from the conversions of only at most ca. 89%.

EP-A 0 745 582 describes a simple and economical synthesis route for glycine-N,N-diacetic acids such as MGDA, starting from cost-effective starting materials, as far as possible without interconnected purification steps, where the highest possible overall yield coupled with simultaneously high product purities, with low NTA contents, as far as possible below 2% by weight, is desired, by Strecker synthesis in aqueous medium at a pH of 0 to 11 and subsequent saponification, where the starting material used is raw material originating from the technical synthesis of glycine derivatives or precursors thereof, or of iminodiacetonitrile or iminodiacetic acid, which raw material has not been purified, i.e. has generally not been isolated as solid or, for example, freed from secondary constituents by crystallization, or mother liquors produced during such syntheses.

Accordingly, it was an object of the present invention to provide a further improved process for the preparation of MGDA trialkali metal salts by Strecker synthesis which is characterized in particular by a further increased space-time yield and also further reduced contents of toxic secondary components, in particular of NTA, below 0.1% by weight of NTA, based on a 40% strength by weight aqueous MGDA trialkali metal salt solution.

The object is achieved by a process for the preparation of aqueous solutions of MGDA trialkali metal salts with high yield and purity by Strecker synthesis, starting from an aqueous solution of α-alanine, by reaction with formaldehyde and hydrocyanic acid in aqueous solution to give the α-alanine-N,N-diacetonitrile and saponification thereof with a base to give the corresponding methylglycine-N,N-diacetic acid trialkali metal salt, where the α-alanine is partially neutralized and the addition of formaldehyde and hydrocyanic acid for the conversion to the α-alanine-N,N-diacetonitrile is controlled such that the concentration of free hydrocyanic acid in the liquid reaction mixture at any time is limited such that secondary reactions, in particular to give formaldehyde cyanohydrin, including consecutive reactions of formaldehyde cyanohydrin, and also the polymerization of hydrocyanic acid take place only insofar as the specification requirements for methylglycine-N,N-diacetic acid trialkali metal salt, in particular as regards nitrilotriacetic acid content and color, are observed.

In another embodiment, the object is achieved by a process for the preparation of aqueous solutions of methylglycine-N,N-diacetic acid trialkali metal salts by Strecker synthesis, starting from an aqueous solution of α-alanine, by reaction with formaldehyde and hydrocyanic acid to give α-alanine-N,N-diacetonitrile in one reaction unit and saponification thereof with a base to give the aqueous solution of the corresponding methylglycine-N,N-diacetic acid trialkali metal salt, wherein the α-alanine is partially neutralized and the addition of the formaldehyde and the hydrocyanic acid for the conversion to the α-alanine-N,N-diacetonitrile is controlled such that the concentration of free hydrocyanic acid in the aqueous reaction mixture at any time limits such that secondary reactions, in particular to give formaldehyde cyanohydrin, including consecutive reactions of formaldehyde cyanohydrin, and also the polymerization of hydrocyanic acid take place only insofar as the aqueous solution of the methylglycine-N,N-diacetic acid trialkali metal salt at a concentration of 40% by weight of the methylglycine-N,N-diacetic acid trialkali metal salt, based on the total weight of the aqueous methylglycine-N,N-diacetic acid trialkali metal salt solution, has a nitrilotriacetic acid trialkali metal salt content of less than 0.1% by weight.

The inventors have recognized that it is possible, through partial neutralization of the amino acid α-alanine, to start from significantly increased concentrations of this feed material in the aqueous solution which is subjected to the Strecker synthesis, and to thereby significantly increase the space-time yield. Compared with the solubility limit of the free amino acid α-alanine at room temperature of ca. 18% by weight, based on the total weight of the solution, as a result of partial neutralization, it is possible to achieve concentrations of partially neutralized α-alanine in water of up to 40% by weight of α-alanine, or also of up to 50% by weight of α-alanine, based on the total weight of the aqueous solution, with a corresponding increase in the space-time yield.

However, if the Strecker synthesis were to be carried out in a manner known otherwise but starting from partially neutralized α-alanine, then the higher pH would increase the rate of secondary reactions, in particular those which lead to the formation of toxic NTA, and also the undesired polymerization of hydrocyanic acid, which leads to an undesired dark color of the product.

Surprisingly, however, it has been found that these undesired secondary reactions can be limited, meaning that the specification requirements for MGDA trialkali metal salt, in particular as regards NTA content and color, are observed, by controlling the addition of formaldehyde and hydrocyanic acid for the conversion to give α-alanine-N,N-diacetonitrile in such a way that the concentration of free hydrocyanic acid in the liquid reaction mixture is limited in a suitable manner.

The specification requirements for MGDA trialkali metal salt with regard to NTA content and color are generally known:

Thus, the amount of potentially carcinogenic NTA (suspicion of cancer-causing effect) in a ca. 40% strength by weight aqueous MGDA-$Na_3$ salt solution should be less than 0.1% by weight (compare e.g. "Technical Bulletin—Trilon®M Liquid Chelating Agent", BASF 2009).

The product specification for Trilon®M liquid with regard to the color is likewise generally known and provides for a Hazen color number in accordance with DIN EN 1557 of at most 350 (compare "Technical Information Trilon®M grades", BASF edition April 2011, page 4).

Preferably, the hydrocyanic acid is metered into the liquid reaction mixture such that the concentration of free hydrocyanic acid in the liquid reaction mixture is at no time 10 mol %, based on the amount of added hydrocyanic acid, preferably 5 mol %, based on the amount of added hydrocyanic acid.

The maximum permissible concentration of free hydrocyanic acid in the liquid reaction mixture can also be based on the added partially neutralized α-alanine, and should then not exceed 20 mol %, preferably 10 mol %, of free hydrocyanic acid, based on the amount of added partially neutralized α-alanine.

The reaction of partially neutralized α-alanine with hydrocyanic acid and formaldehyde by Strecker synthesis requires a stoichiometric molar ratio of 1 mol of α-alanine to in each case 2 mol of hydrocyanic acid and 2 mol of formaldehyde. In practice, a molar ratio of α-alanine to hydrocyanic acid, and also of α-alanine to formaldehyde of in each case 1.95 to 2.4, preferably 2.0 to 2.2, is generally used.

In a preferred embodiment of the process, the addition of the formaldehyde and of the hydrocyanic acid for the conversion to the α-alanine-N,N-diacetonitrile is controlled such that the concentration of free hydrocyanic acid in the aqueous reaction mixture at any time is limited such that secondary reactions, in particular to give formaldehyde cyanohydrin, including consecutive reactions of formaldehyde cyanohydrin, and also the polymerization of hydrocyanic acid take place only insofar as the aqueous solution of the methylglycine-N,N-diacetic acid trialkali metal salt has a Hazen color number of less than 800, preferably of less than 600, particularly preferably of less than 500.

In a further preferred embodiment, the aqueous solution of the methylglycine-N,N-diacetic acid trialkali metal salt is subjected, in a further process step, to an after-bleaching, giving an aqueous solution of the methylglycine-N,N-diacetic acid trialkali metal salt with a Hazen color number of less than 350, preferably of less than 300.

The after-bleaching (=finish) can take place by a chemical and/or a physical operation. The chemical operation can be oxidative, for example with hydrogen peroxide or air, or reductive, for example with sodium dithionite or sodium hydride. Physically, the after-bleaching can be carried out by absorption of colored components, for example on activated carbon.

The after-bleaching is particularly preferably carried out using aqueous hydrogen peroxide solutions.

The after-bleaching of the aqueous MGDA trialkali metal salt solutions with hydrogen peroxide can be carried out in stages or continuously.

Thus, for example, the hydrogen peroxide solution can be metered, with efficient stirring, into an initial charge of MGDA trialkali metal salt solution in a stirred reactor or in a pumped product circulation. Amounts, temperatures and residence times are preferred as follows:

In general, very small amounts of hydrogen peroxide suffice, in particular 1 to 5 kg, preferably 1 to 3 kg of hydrogen peroxide (calculated as 100% $H_2O_2$) per 1000 liters of 40% strength MGDA trialkali metal salt solution (corresponding to ca. 1300 kg).

Preference is given to using 10 to 50% strength aqueous hydrogen peroxide solution, particularly preferably 30% strength aqueous hydrogen peroxide solution, so-called perhydrol.

Preference is given to temperatures between 20 and 80° C., further preferably between 30 and 70° C., particularly preferably between 40 and 65° C. Preferred residence times are between 10 and 180 minutes, particularly preferably between 15 and 120 minutes.

In another embodiment, crystalline α-alanine is used as feed material, which is dissolved or suspended in water and is then partially neutralized in the manner described above and converted to the MGDA trialkali metal salt.

The partial neutralization of the α-alanine can be carried out in particular with sodium hydroxide or potassium hydroxide or a mixture of sodium hydroxide and potassium hydroxide. In particular, the neutralization of the α-alanine can be carried out to a degree of neutralization of from 40 to 90%, preferably from 50 to 85%, particularly preferably from 60 to 80%. Here, concentrated aqueous solutions are obtained which preferably comprise 20 to 50% by weight of α-alanine, further preferably 25 to 40% by weight of α-alanine, based on the total weight of the aqueous solution.

In a first process variant, partially neutralized α-alanine is reacted in aqueous solution with formaldehyde and hydrocyanic acid to give an aqueous solution of α-alanine-N,N-diacetonitrile in such a way that hydrocyanic acid is introduced into the liquid reaction mixture in a later operation compared with the two other reactants, partially neutralized α-alanine and formaldehyde.

Here, it is possible to operate in particular either batchwise (semi-batch) or continuously.

According to a first preferred process variant, in semi-batch procedure, partially neutralized aqueous α-alanine is introduced into a reactor as initial charge, and formaldehyde and also hydrocyanic acid are metered in parallel, the metered addition of the hydrocyanic acid being slower in terms of time compared with formaldehyde.

In a second process variant, partially neutralized α-alanine is first reacted with the entire amount of formaldehyde required for the reaction, or a part amount thereof, and the resulting reaction mixture is then metered in with the hydrocyanic acid required for the reaction by itself or with hydrocyanic acid and the remaining amount of formaldehyde, in parallel.

In a further preferred process variant, the Strecker synthesis is carried out continuously, preferably in a cascade of two or more reaction zones connected in series.

The two or more reaction zones connected in series can in each case be different reaction zones in a single reactor or individual reactors.

Preferably, in a first reaction zone, partially neutralized α-alanine, separately or premixed with the entire amount of formaldehyde required for the reactions on its own or additionally with a part amount of the hydrocyanic acid required for the reaction, is metered in in parallel. In a subsequent reaction zone, the resulting reaction mixture from the first reaction zone is metered in in parallel with the entire amount of hydrocyanic acid required for the reaction or with the remaining amount of hydrocyanic acid.

The saponification of the aqueous solutions of α-alanine-N,N-diacetonitrile obtained by Strecker synthesis is advantageously carried out by firstly saponifying with sodium hydroxide solution or potassium hydroxide solution or a mixture of sodium hydroxide solution and potassium hydroxide solution at a temperature in the range from 20 to 80° C., preferably at a temperature in the range from 30 to 70° C., and then at temperatures≥90° C. to give aqueous MGDA trialkali metal salt solutions. In the process, during the saponification at temperatures≥90° C., the reaction solution is simultaneously freed from ammonia.

The saponification can likewise be carried out either in stages (semi-batch) or continuously.

In one preferred process variant, the L-enantiomer of α-alanine is used as starting material.

The L-enantiomer of α-alanine is available at low cost and leads, through Strecker synthesis, as a result of reaction with hydrocyanic acid and formaldehyde in aqueous solution, to L-α-alanine-N,N-diacetonitrile, and saponification thereof with a base leads to aqueous solutions which not only have a higher saturation concentration of the L-enantiomer compared to the D,L-racemate of the MGDA trialkali metal salts, but which also produce a readily crystallizing solid by means of crystallization.

The advantages of the higher solubility of L-MGDA trialkali metal salt compared to the racemate are that the synthesis, the storage, the sale and the transportation of more highly concentrated solutions is possible, and as a result cost savings are achieved through, for example, improved space-time yields, lower-volume synthesis and storage containers, and also reduced transportation or energy costs, e.g. during spray-drying processes.

The invention is illustrated in more detail below by reference to working examples.

COMPARATIVE EXAMPLE 1

(Semi-batch; Degree of Neutralization 0, Alanine Concentration Ca. 18%; Excesses of HCHO And HCN in Each Case 0.03 Equivalents)

Over the course of 1 hour, 203 g of 30% strength formaldehyde (2.03 mol) and 54.8 g (2.03 mol) of hydrocyanic acid were added in parallel at 30° C. with cooling to a solution of 89 g (1.0 mol) of α-alanine in 405 g of water (ca. 18% strength). The mixture was then after-stirred for 1 hour at 30° C.

Total cyanide, i.e. sum of free, unreacted HCN and of cyanide bonded in the formaldehyde cyanohydrin 0.32% (analytical procedure=potentiometric titration); HCN conversion from potentiometric titration of the free HCN 96%, pH 1.7.

245 g of 50% strength sodium hydroxide solution (3.06 mol) were introduced as initial charge in a stirred flask, and the above α-alanine-N,N-diacetonitrile (ADAN) solution was metered in over the course of 1 hour at 27 to 36° C. with cooling. The mixture was then stirred further for 60 minutes at ca. 30° C. The mixture was then heated to 95 to 102° C. and the saponification was completed within ca. 3 hours.

This resulted in 635 g of a 39.8% strength (according to HPLC evaluation) solution of MGDA trisodium salt, with an NTA-Na3 content of 0.20%, and with a Hazen color number of 850, which does not correspond to the specification requirements, and a yield of 93.2%.

COMPARATIVE EXAMPLE 2

(Semi-batch; as Comparative Example 1, but with 100% Alanine Degree of Neutralization, Alanine Concentration ca. 40%)

89 g (1.0 mol) of α-alanine were introduced into 55 g of water. With cooling, the mixture was completely neutralized with 80 g of 50% strength sodium hydroxide solution (1.0 mol) (ca. 40% strength alanine); initial pH value 13.7.

At ca. 30° C., with cooling for 1 hour, 203 g of 30% strength formaldehyde (2.03 mol) and 54.8 g (2.03 mol) of hydrocyanic acid were metered in. The mixture was then after-stirred for 1 hour at 30° C.

Analysis of the resulting ADAN solution: total cyanide 2.86%, HCN conversion 60.5%, final pH 8.0.

165 g of 50% strength sodium hydroxide solution (2.06 mol) were introduced. To this was added, at 30-35° C., the above ADAN solution over the course of 1 hour with cooling. The mixture was then further stirred for 60 minutes at ca. 30° C. The mixture was then heated to 95-102° C. and the saponification was completed over the course of ca. 4 hours. This resulted in 482 g of a 38.6% strength (according to HPLC evaluation) solution of MGDA trisodium salt, with an NTA-Na3 content of 5.1% (not on-spec). Yield of MGDA-Na3: 68.6%, Hazen color number substantially higher than 1000.

COMPARATIVE EXAMPLE 3

(Semi-batch; as Comparative Example 2, but with 85% Strength Alanine Degree of Neutralization, Alanine Concentration ca. 42%)

89 g (1.0 mol) of α-alanine were introduced into 55 g of water. With cooling, the mixture was partially neutralized with 68 g of 50% strength sodium hydroxide solution (0.85 mol). Initial pH: 11.5. At ca. 30° C., 203 g of 30% strength formaldehyde (2.03 mol) and 54.8 g (2.03 mol) of hydrocyanic acid were metered in with cooling over the course of 1 hour. The mixture was then after-stirred for 1 hour at 30° C.

Analysis of the resulting ADAN solution: total cyanide 0.24%, HCN conversion 98%. Final pH 4.5.

The saponification was carried out as in comparative example 2 with 176.8 g of 50% strength sodium hydroxide solution (2.21 mol).

This resulted in 657 g of a 40.3% strength MGDA-Na3 solution with an NTA-Na3 content of 0.12%.

Yield of MGDA-Na3: 97.7% with regard to alanine, Hazen color number >1000.

COMPARATIVE EXAMPLE 4

(Semi-batch, as Example 1, but with Alanine Degree of Neutralization 65%, Alanine Concentration Ca. 30%)

133.5 g (1.5 mol) of α-alanine were introduced into 230 g of water. The mixture was partially neutralized with cooling with 78 g of 50% strength sodium hydroxide solution (0.975 mol). At 40° C., in parallel 82.3 g (3.05 mol) of HCN and 305 g of 30% strength formaldehyde (3.05 mol) were metered in over the course of 1 h, and the mixture was after-stirred for 1 h at 40° C.

Analysis: total cyanide 0.23%. HCN conversion 98%. Final pH 3.9.

The saponification was carried out analogously to comparative example 2 with 288.8 g of 50% strength sodium hydroxide solution (3.61 mol).

This gave 903 g of a 43.2% strength MGDA-Na3 solution with an NTA-Na3 content of 0.15%.

Yield of MGDA-Na3: 96%, Hazen color number 900.

COMPARATIVE EXAMPLE 5

(Semicontinuous Procedure: Parallel Metered Addition of all 3 Components with 18% Strength Alanine, Degree of Neutralization 0)

General procedure: a small amount of water was initially introduced in the stirred reactor. Then, in parallel, the 3 reactants were metered in over the course of 60 minutes at 40° C. After-reaction for 1 hour.

Analogously, for the saponification, a small amount of NaOH (ca. 10%) was initially introduced and the large remainder of NaOH and also the ADAN solution were metered in in parallel at ca. 30-35° C. over the course of 1 hour. After-reaction and final saponification were carried out as under semi-batch conditions. MGDA-Na3 yield: 92.1% with regard to alanine; NTA-Na3 content of a 40.1% strength MGDA-Na3 solution: 0.24%, Hazen color number 950.

COMPARATIVE EXAMPLE 6

(Semicontinuous Procedure, as Comparative Example 5, but with 30% Strength Alanine Concentration, Degree of Neutralization Ca. 70%)

MGDA-Na3 yield: 92.7% with regard to alanine; NTA-Na3 content of a 39.9% strength MGDA-Na3 solution: 0.17%, Hazen color number>1000.

COMPARATIVE EXAMPLE 7

(Continuous Procedure/Stirred-reactor Cascade—without Hydrocyanic Acid Split)

The continuous preparation of a ca. 40% strength MGDA-Na3 solution was carried out in an apparatus consisting of in each case 3 stirred reactors at 40° C. in the nitrile stage (R1, R2 and R3) and 40° C. in the saponification stage (R4, R5, R6). The saponification was then completed in stirred reactor R7 at 105-110° C., as well as a final ammonia stripping. HCN, formaldehyde and a solution of alanine (65% partially neutralized with sodium hydroxide solution, 30% content based on alanine) were added to R1, the hydroxide solution to R4. The molar ratios of the feed materials were selected as in comparative example 4. The metered addition is carried out such that the residence times in R1-R2-R3 are 55-80 minutes, in R3-R6 are 200-280 minutes and in R7 are 150-200 minutes. The product typically has an NTA-Na3 content of 0.25-0.40% and Hazen color numbers of >1000.

MGDA-Na3 yield: 92-93% with regard to alanine.

EXAMPLE 1

(Semi-batch, as Comparative Example 4, but with More Rapid Formaldehyde Metered Addition Versus HCN)

In contrast to comparative example 4, formaldehyde was metered in in 30 minutes, HCN was metered in in 60 minutes.

MGDA-Na3 yield: 98.1% with regard to alanine; NTA-Na3 content in the 40.4% strength MGDA-Na3 solution: 0.06%, Hazen color number 320.

EXAMPLE 2

(With After-bleaching)

With vigorous stirring, 10 g of a 30% strength hydrogen peroxide solution were metered into the solution obtained according to example 1 over the course of 15 minutes at ca. 60° C. The mixture was then stirred further for ca. 30 minutes at 60° C. The resulting solution had a Hazen color number of 180.

EXAMPLE 3

(Semi-batch, Alanine Concentration 30%, Degree of Neutralization ca. 70%).

89 g (1.0 mol) of α-alanine were introduced into 150 g of water. With cooling, the mixture was partially neutralized with 56 g of 50% strength sodium hydroxide solution (0.7 mol).

At 40° C., in parallel at ca. 40° C., 203 g of 30% strength formaldehyde (2.03 mol) were metered in over the course of 60 minutes and 54.8 g (2.03 mol) of hydrocyanic acid were metered in over the course of 90 minutes.

The mixture was then after-stirred for 30 minutes at 40° C.

Analysis of the resulting ADAN solution: total cyanide 0.29%, HCN conversion 99%, final pH 4.1.

189 g of 50% strength sodium hydroxide solution (2.36 mol) were introduced. At 45-50° C., the above ADAN solution was added to this over the course of 1 hour. The mixture was then further stirred for 60 minutes at 50° C.

Then, at 95-102° C., the saponification and also the ammonia distillation were completed over the course of ca. 3 hours.

This resulted in 665 g of a ca. 39.5% strength MGDA-Na3 solution.

Yield: 97.0%—NTA-Na3 content 0.08%—Hazen color number 340.

EXAMPLE 4

(Semicontinuous Procedure, as Comparative Example 4, but with More Rapid Metered Addition of Alanine and Formaldehyde in 30 Minutes, Hydrocyanic Acid Addition in 60 Minutes)

Best result: MGDA-Na3 yield: 97.6%—NTA-Na3 content of a 40.3% strength ADA-Na3 solution: 0.03%, Hazen color number 330.

EXAMPLE 5

The solution obtained according to example 4 was bleached under the conditions of example 2. This resulted in a Hazen color number of 150.

EXAMPLE 6

(Semicontinuous Procedure, as Comparative Example 4, but with Hydrocyanic Acid Split 30%)

Ca. 30% strength alanine with degree of neutralization 70%, formaldehyde and only 70% of the total amount of hydrocyanic acid were metered in over the course of 60 minutes in parallel at 40° C. The resulting reaction mixture was then discharged without post-reaction and immediately metered in in parallel with the remaining 30% of hydrocyanic acid over the course of 60 minutes. The mixture was further stirred for 30 minutes at 40° C.

The saponification was carried out as in comparative example 5.

MGDA-Na3 yield: 96.6%—NTA-Na3 content: 0.07%, Hazen color number 370.

EXAMPLE 7

(Semicontinuous Procedure, as Example 6, with 30% Strength Alanine Concentration, Degree of Neutralization Ca. 70%, but with Hydrocyanic Acid Split 50%)

MGDA-Na3 yield: 97.3%—NTA-Na3 content of a 39.9% strength MGDA-Na3 solution: 0.05%, Hazen color number 320.

EXAMPLE 8

(Continuous Procedure/Stirred-reactor Cascade—with Hydrocyanic Acid Split)

The continuous preparation of a ca. 40% strength MGDA-Na3 solution was carried out as in comparative example 7, where, however, the metered addition of the HCN also took place into R2 and the added amount of HCN was divided in the ratio 4:1 between R1 and R2. The product typically has an NTA-Na3 content of <0.1% and Hazen color numbers of 450-650.

MGDA-Na3 yield: 97-98.5% with regard to alanine.

EXAMPLE 9

(With After-bleaching)

The solution obtained in example 8 was then bleached in a residence-time section by metering in 30% strength hydrogen peroxide (ca. 5 liters per 1 m3 of solution) at 40-50° C. and completion of the reaction in a residence-time container.

This typically resulted in Hazen color numbers of <300.

EXAMPLE 10

Preparation of a ca. 50% Strength by Weight L-MGDA-Na3 Solution (Analogous to Example 8, but L-α-Alanine was Used as Alanine Source)

In the last stage of the saponification at 95-102° C., the ammonia formed and enough water were distilled off such that ultimately a ca. 50% strength by weight solution of L-MGDA-Na3 salt resulted.

Yield of L-MGDA-Na3: 97.0%, based on L-alanine. NTA-Na3 content: 0.08%.

Hazen color number 270.

A pale-colored, highly concentrated (50% strength by weight) complexing agent solution with a very low residual content of NTA is thus obtained.

We claim:

1. A process for preparing an aqueous solution of a methylglycine-N,N-diacetic acid trialkali metal salt by Strecker synthesis, the process comprising, in one reaction unit:

reacting α-alanine with formaldehyde and hydrocyanic acid in an aqueous solution to obtain α-alanine-N,N-diacetonitrile and saponifying the α-alanine-N,N-diacetonitrile with a base to obtain a methylglycine-N,N-diacetic acid trialkali metal salt, wherein the α-alanine is partially neutralized, in the reaction the hydrocyanic acid is added to a solution of the α-alanine and formaldehyde in water and the addition of hydrocyanic acid is controlled so that the concentration of free hydrocyanic acid in the aqueous reaction mixture at any time is low and unwanted secondary reactions of formaldehyde cyanohydrin and polymerization of hydrocyanic acid are limited to take place only insofar as specification requirements for methylglycine-N,N-diacetic acid trialkali metal salt are observed.

2. A process for preparing an aqueous solution of a methylglycine-N,N-diacetic acid trialkali metal salt by Strecker synthesis, the process comprising, in one reaction unit:

reacting α-alanine with formaldehyde and hydrocyanic acid in an aqueous solution to obtain α-alanine-N,N-diacetonitrile and saponifying the α alanine-N,N-diacetonitrile with a base to obtain an aqueous solution of methylglycine-N,N-diacetic acid trialkali metal salt, wherein the α-alanine is partially neutralized, in the reaction the hydrocyanic acid is added to a solution of the α-alanine and formaldehyde in water and the addition of hydrocyanic acid is controlled so that the concentration of free hydrocyanic acid in the aqueous reaction mixture at any time is low and unwanted secondary reactions of formaldehyde cyanohydrin and polymerization of hydrocyanic acid are limited to take place only insofar as the aqueous solution of the methylglycine-N,N-diacetic acid trialkali metal salt has a nitrilotriacetic acid trialkali metal salt content of less than 0.1% by weight at a concentration of 40% by weight of the methylglycine-N,N-diacetic acid trialkali metal salt, based on the total weight of the aqueous methylglycine-N,N-diacetic acid trialkali metal salt solution.

3. The process according to claim 1, wherein the addition of hydrocyanic acid is controlled so that the concentration of free hydrocyanic acid in the aqueous reaction mixture at any time is limited such that secondary reactions take place only insofar as the aqueous solution of the methylglycine-N,N-diactic acid trialkali metal salt has a Hazen color number of less than 800.

4. The process according to claim 1, wherein the aqueous solution of the methylglycine-N,N-diacetic acid trialkali metal salt is subjected to an after-bleaching, giving an aqueous solution of the methylglycine-N,N-diacetic acid trialkali metal salt with a Hazen color number of less than 350.

5. The process according to claim 1, the process further comprising:

dissolving or suspending crystalline α-alanine in water to obtain a water mixture of the α-alanine; and partially neutralizing the water mixture with a base to obtain the aqueous solution of α-alanine.

6. The process according to claim 1, wherein partial neutralization of the α-alanine is carried out with sodium hydroxide or potassium hydroxide or a mixture of sodium hydroxide solution and potassium hydroxide solution to a degree of neutralization of from 40 to 90% to give a concentrated aqueous solution comprising 20 to 50% by weight of alanine based on the total weight of the aqueous solution.

7. The process according to claim 1, the process further comprising:
charging the partially neutralized α-alanine and the formaldehyde into the reaction unit; and in a later operation, introducing the hydrocyanic acid into the reaction unit.

8. The process according to claim 1, the process further comprising, as a semi-batch process:
introducing partially neutralized aqueous α-alanine as initial charge in a reaction unit, and
metering in formaldehyde and hydrocyanic acid in parallel, wherein metered addition of the hydrocyanic acid takes place more slowly in terms of time compared with the formaldehyde.

9. The process according to claim 1,
wherein the reaction of partially neutralized α-alanine with formaldehyde and hydrocyanic acid is carried out continuously, in a cascade of two or more reaction zones connected in series.

10. The process according to claim 9,
wherein the two or more reaction zones are in each case individual reactors.

11. The process according to claim 9,
wherein the two or more reaction zones are in each case different zones within a single reactor.

12. The process according to claim 10,
wherein partially neutralized α-alanine, separately or premixed with an entire amount of formaldehyde required for the reacting, on its own or additionally with a part amount of the hydrocyanic acid required for the reacting, is metered into a first reaction zone in parallel and, in a subsequent reaction zone, the entire amount of the hydrocyanic acid required for the reacting or the remaining amount of hydrocyanic acid, in parallel or premixed, is metered into the reaction mixture resulting from the first reaction zone.

13. The process according to claim 1,
wherein saponifying is carried out such that firstly conversion is carried out with sodium hydroxide solution or potassium hydroxide solution or a mixture of sodium hydroxide solution and potassium hydroxide solution at 20 to 80°C., and then at a temperature ≥90°C., with release of ammonia to obtain the aqueous methylglycine-N,N-diacetic acid trialkali metal salt.

14. The process according to claim 1, wherein the α-alanine is L-α-alanine.

15. The process according to claim 3,
wherein the Hazen color number is of less than 600.

16. The process according to claim 3,
wherein the Hazen color number is of less than 500.

17. The process according to claim 4,
wherein the Hazen color number is of less than 300.

18. The process according to claim 6,
wherein the partial neutralization of the α-alanine is carried out with sodium hydroxide or potassium hydroxide or the mixture of sodium hydroxide solution and potassium hydroxide solution to a degree of neutralization of from 50 to 85% to give a concentrated aqueous solution comprising 25 to 40% by weight of alanine based on the total weight of the aqueous solution.

19. The process according to claim 6,
wherein the partial neutralization of the α-alanine is carried out with sodium hydroxide or potassium hydroxide or the mixture of sodium hydroxide solution and potassium hydroxide solution to a degree of neutralization of from 60 to 80% to give a concentrated aqueous solution comprising 20 to 50% by weight of alanine based on the total weight of the aqueous solution.

20. The process according to claim 13,
wherein the saponifying is carried out at 30 to 70°C., and then at a temperature equal to or greater than 90°C., with release of ammonia to obtain the aqueous methylglycine-N,N-diacetic acid trialkali metal salt.

* * * * *